United States Patent [19]

Hamprecht

[11] 4,219,499
[45] Aug. 26, 1980

[54] SULFAMIC ACID HALIDES

[75] Inventor: Gerhard Hamprecht, Mannheim, Fed. Rep. of Germany

[73] Assignee: BASF Aktiengesellschaft, Fed. Rep. of Germany

[21] Appl. No.: 911,363

[22] Filed: Jun. 1, 1978

Related U.S. Application Data

[62] Division of Ser. No. 807,064, Jun. 16, 1977, Pat. No. 4,131,620.

[30] Foreign Application Priority Data

Jul. 31, 1976 [DE] Fed. Rep. of Germany ....... 2634485

[51] Int. Cl.² ............................................ C07C 155/00
[52] U.S. Cl. ................................................. 260/543 R
[58] Field of Search ............................ 260/543 R, 543

[56] References Cited

U.S. PATENT DOCUMENTS

| 3,919,308 | 11/1975 | Hamprecht | 260/543 R |
| 3,946,048 | 3/1976 | Fischer et al. | 260/346.2 R |
| 3,963,668 | 6/1976 | Wurmb et al. | 260/37 AL |
| 3,992,444 | 11/1976 | Hamprecht et al. | 260/543 R |
| 4,014,931 | 3/1977 | Hamprecht | 260/543 R |
| 4,043,863 | 8/1977 | Bjorklund et al. | 260/543 R |
| 4,049,709 | 9/1977 | Hamprecht et al. | 260/543 R |

*Primary Examiner*—Bernard Helfin
*Attorney, Agent, or Firm*—Keil & Witherspoon

[57] ABSTRACT

New sulfamic acid halides and a process for their manufacture by reacting N-(α-haloalkyl)-sulfamic acid halides with alcohols. The products are starting materials for the manufacture of crop protection agents, dyes and pharmaceuticals.

9 Claims, No Drawings

SULFAMIC ACID HALIDES

This is a division of application Ser. No. 807,064, filed June 16, 1977, and now U.S. Pat. No. 4,131,620.

The present invention relates to new sulfamic acid halides and to a process for their manufacture by reacting N-(α-haloalkyl)-sulfamic acid halides with alcohols.

The manufacture of N-alkylamidosulfonyl chlorides by reacting monoalkylammonium chlorides with sulfuryl chloride has been disclosed (Acta chem. Scand., 17 (1963), 2,141). When carrying out the reaction in the presence of a strongly polar, organic solvent, with addition of a metal halide catalyst, the yields of the reaction can be improved by adopting the method described in German Pat. No. 1,242,627. Whilst good yields of lower, non-branched alkylamidosulfonyl chlorides are thus obtained, the yields decrease substantially with branching and increasing chain length of the alkyl radical. Furthermore, α-alkoxyalkylaminosulfonyl halides cannot be manufactured by this method. The long reaction time which the process requires to give a satisfactory yield is a disadvantage. The above methods present processing difficulties, particularly on an industrial scale, as well as presenting problems of protection of the environment, because of the high chlorine content of the by-products.

German Laid-Open Application DOS 2,408,530 discloses a process for the manufacture of N-alkoxyalkyl-N-β-haloalkylsulfamic acid halides by reacting N-alkoxyalkyl-aziridines with sulfuryl halides. However, α-alkoxyalkyl-alkylsulfamic acid halides which are not substituted by halogen in the β-position can again not be manufactured by this process.

The manufacture of N,N-dimethylaminosulfonyl chloride by reacting sulfuryl chloride with dimethylamine has been disclosed (Chemische Berichte, 14 (1881), 1,810–1,812). The process is involved and uneconomical, particularly on an industrial scale, and gives unsatisfactory yields. It cannot be used to manufacture α-alkoxyalkyl compounds.

German Published Application DAS No. 1,028,129 discloses the manufacture of N,N-dialkylsulfamic acid chlorides by reacting secondary N-chloramines with sulfur dioxide. However, alkyl derivatives substituted by alkoxy groups in the α-position can again not be obtained by this process, since the reaction with sulfur dioxide is difficult to carry out industrially, because of the chloramines tending to decompose vigorously.

I have found that sulfamic acid halides of the formula

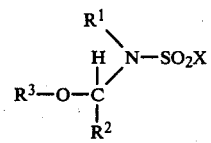

where $R^1$ is an aliphatic or cycloaliphatic radical, $R^2$ is hydrogen or an aliphatic radical, $R^3$ is an aliphatic, cycloaliphatic or araliphatic radical and X is halogen, are obtained in an advantageous manner when N-(α-haloalkyl)-sulfamic acid halides of the formula

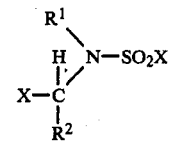

where $R^1$, $R^2$ and X have the above meanings, are reacted with an alcohol of the formula

$$R^3—OH \qquad III$$

where $R^3$ has the above meanings.

Further, I have found the new sulfamic acid halides of the formula

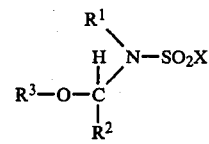

where $R^1$ is an aliphatic or cycloaliphatic radical, $R^2$ is hydrogen or an aliphatic radical, $R^3$ is an aliphatic, cycloaliphatic or araliphatic radical and X is halogen, but, if $R^1$ is vinyl which is unsubstituted or substituted by halogen and/or aliphatic radicals in the β-position to the nitrogen, or is an aliphatic radical substituted by halogen in the α-position of β-position, $R^3$ is a cycloaliphatic or araliphatic radical.

Further, I have found that the preferred new sulfamic acid halides are those of the formula

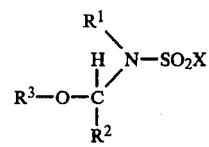

where $R^1$ is alkyl of 1 to 20 carbon atoms which may be unsubstituted or substituted by one or more chlorine and/or bromine atoms in the β-, γ- and/or δ-position to the nitrogen, or is cycloalkyl of 4 to 8 carbon atoms, $R^2$ is hydrogen or is alkyl of 1 to 18 carbon atoms which is unsubstituted or substituted by one or more chlorine and/or bromine atoms in the β-, γ- and/or δ-position to the nitrogen, $R^3$ is alkyl of 1 to 20 carbon atoms which is unsubstituted or substituted by 1 or 2 ether groups and/or 1 or 2 chlorine atoms and/or bromine atoms, or is alkenyl or alkynyl, of 2 to 20 carbon atoms, which are unsubstituted or substituted by 1 or 2 ether groups and/or 1 or 2 chlorine atoms and/or bromine atoms, or is cycloalkyl of 4 to 8 carbon atoms which is unsubstituted or substituted by one chlorine atom or is aralkyl of 7 to 12 carbon atoms, and X is chlorine or bromine, but if $R^1$ is an aliphatic radical which is substituted by halogen in the β-position, $R^3$ is a cycloaliphatic or araliphatic radical.

Where N-chloromethyl-N-ethylsulfamic acid chloride and n-propanol are used, the reaction can be represented by the following equation:

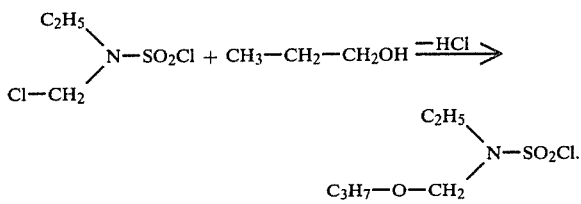

Compared to the prior art, the process of the invention gives the new N,N-disubstituted sulfamic acid halides, which are substituted in the α-position by optionally substituted and/or unsaturated alkoxy, cycloalkoxy or aralkoxy, in a simple and economical manner, and in good yield and high purity. The reaction time is short and the working up of the reaction mixture is simple, particularly from the point of view of protection of the environment, and safe. Starting materials II where alkyl contains a fairly high number of carbon atoms may also be converted by the process of the invention. All these advantageous results are surprising in view of the prior art. The high reactivity and selectivity of the halogen atom of the α-haloalkyl group was unforeseeable, since a reaction at the sulfonyl halogen atom would have been expected when using excess starting material III.

Preferred starting materials II and III and accordingly preferred end products I are those where $R^1$ is straight-chain or branched alkyl of 1 to 20, especially of 1 to 8, carbon atoms, which is unsubstituted or substituted by one or more halogens, especially chlorine and/or bromine, in the β-, γ- and/or δ-position to the nitrogen, or cycloalkyl of 4 to 8 carbon atoms, $R^2$ is hydrogen or straight-chain or branched alkyl of 1 to 18, especially of 1 to 8, carbon atoms, which is unsubstituted or substituted by one or more halogens, especially chlorine and/or bromine, in the β-, γ- and/or δ-position to the nitrogen, $R^3$ is straight-chain or branched alkyl of 1 to 20, preferably of 1 to 8, carbon atoms, which is unsubstituted or substituted by 1 or 2 ether groups and/or one or 2 halogens, preferably chlorine or bromine, or is straight-chain or branched alkenyl or alkynyl of 2 to 20, especially of 2 to 8, carbon atoms, which is unsubstituted or substituted by 1 or 2 ether groups and/or 1 or 2 halogens, preferably chlorine or bromine, or is cycloalkyl of 4 to 8 carbon atoms which is unsubstituted or substituted by one chlorine or is aralkyl of 7 to 12 carbon atoms, and X is fluorine or especially chlorine or bromine. The said radicals may in addition be substituted by groups which are inert under the reaction conditions, e.g. alkyl of 1 to 4 carbon atoms or carbalkoxy of 2 to 4 carbon atoms.

Preferred suitable starting materials II are N-chloromethyl-N-methylsulfamic acid chloride, N-chloromethyl-N-ethyl-sulfamic acid chloride, N-chloromethyl-N-n-propylsulfamic acid chloride, N-chloromethyl-N-isopropylsulfamic acid chloride, N-chloromethyl-N-n-butylsulfamic acid chloride, N-chloromethyl-N-isobutylsulfamic acid chloride, N-chloromethyl-N-sec.-butyl-sulfamic acid chloride, N-chloromethyl-N-tert.-butylsulfamic acid chloride, N-chloromethyl-N-pentylsulfamic acid chloride, N-chloromethyl-N-cyclopentylsulfamic acid chloride, N-chloromethyl-N-hexylsulfamic acid chloride, N-chloromethyl-N-cyclohexylsulfamic acid chloride, N-chloromethyl-N-heptylsulfamic acid chloride, N-chloromethyl-N-1,2-dimethylbutyl-(1)-sulfamic acid chloride, N-chloromethyl-N-1,3-dimethylbutyl-(1)-sulfamic acid chloride, N-chloromethyl-N-3-chloropentyl-(1)-sulfamic acid chloride, N-chloromethyl-N-3-chloropropyl-(1)-sulfamic acid chloride, N-chloromethyl-N-4-chloroisoamyl-(1)-sulfamic acid chloride, N-chloromethyl-N-2-chloromethylpropyl-(1)-sulfamic acid chloride, N-chloromethyl-N-2-fluoromethylpropyl-(1)-sulfamic acid fluoride, N-chloromethyl-N-3-fluorobutyl-(1)-sulfamic acid fluoride, N-chloromethyl-N-3-fluoropropyl-(1)-sulfamic acid fluoride, N-chloromethyl-N-4-chloropentyl-(1)-sulfamic acid chloride, N-chloromethyl-N-4-chlorobutyl-(2)-sulfamic acid chloride, N-1-chloroethyl-N-methylsulfamic acid chloride, N-1-chloroethyl-N-ethylsulfamic acid chloride, N-1-chloroethyl-N-n-propylsulfamic acid chloride, N-1-chloroethyl-N-isopropylsulfamic acid chloride, N-1-chloroethyl-N-n-butyl-sulfamic acid chloride, N-1-chloroethyl-N-isobutylsulfamic acid chloride, N-1-chloroethyl-N-sec.-butylsulfamic acid chloride, N-1-chloroethyl-N-tert.-butylsulfamic acid chloride, N-1-chloroethyl-N-pentylsulfamic acid chloride, N-1-chloroethyl-N-cyclopentylsulfamic acid chloride, N-1-chloroethyl-N-hexylsulfamic acid chloride, N-1-chloroethyl-N-cyclohexylsulfamic acid chloride, N-1-chloroethyl-N-heptylsulfamic acid chloride, N-1-chloroethyl-N-1,2-dimethylbutyl-(1)-sulfamic acid chloride, N-1-chloroethyl-N-1,3-dimethylbutyl-(1)-sulfamic acid chloride, N-1-chloroethyl-N-3-chloropentyl-(1)-sulfamic acid chloride, N-1-chloroethyl-N-3-chloropropyl-(1)-sulfamic acid chloride, N-1-chloroethyl-N-4-chloroisoamyl-(1)-sulfamic acid chloride, N-1-chloroethyl-N-2-chloromethylpropyl-(1)-sulfamic acid chloride, N-1-chloroethyl-N-2-fluoromethylpropyl-(1)-sulfamic acid fluoride, N-1-chloroethyl-N-3-fluorobutyl-(1)-sulfamic acid fluoride, N-1-chloroethyl-N-3-fluoropropyl-(1)-sulfamic acid fluoride, N-1-chloroethyl-N-4-chloropentyl-(1)-sulfamic acid chloride, N-1-chloroethyl-N-4-chlorobutyl-(2)-sulfamic acid chloride, the N-(1-chloropropyl), N-(1-chloroisopropyl), N-(1-chlorobutyl), N-(1-chloroisobutyl), N-(1-chloro-sec.-butyl) and N-(1-chloro-tert.-butyl) compounds corresponding to the above N-chloromethyl compounds, and the corresponding sulfamic acid bromides and sulfamic acid fluorides.

Advantageous starting materials III are methanol, ethanol, n-propanol, isopropanol, n-butanol, isobutanol, sec.-butanol, tert.-butanol, cyclopropanol, cyclobutanol, cyclopentanol, n-pentanol, 2-pentanol, 3-pentanol, tert.-amyl alcohol, neopentyl alcohol, 2-methylbutanol, 3-methylbutanol, 3-methyl-2-butanol, n-hexanol, 4-methyl-2-pentanol, 2,3-dimethylbutanol, 2-methyl-1-pentanol, 2-hexanol, 3-hexanol, 3-methyl-2-pentanol, 3-methylpentanol, 4-methylpentanol, 3-methyl-3-pentanol, 4,4-dimethylbutanol, cyclohexanol, n-heptanol, 2-heptanol, 3-heptanol, 4-heptanol, cycloheptanol, octanol, nonanol, decanol, undecanol, dodecanol, tridecanol, tetradecanol, pentadecanol, hexadecanol, heptadecanol, octadecanol, nonadecanol, eicosanol, 2-chloroethanol, 2-fluoroethanol, 1-chloropropanol, 2-chloropropanol, 3-chloropropanol, 1-chloro-2-propanol, 2-chlorobutanol, 1-chloroethanol, 2-chloro-2-methyl-3-propanol, 2-fluoropropanol, 3-fluoropropanol, 2-bromoethanol, 2-chlorocyclohexanol, 1,1,1-trifluoroisopropanol, allyl alcohol, methallyl alcohol, crotyl alcohol, 2-methylbut-1-en-3-ol, but-1-yn-3-ol, but-2-yn-1-ol, but-1-en-3-ol, propargyl alcohol, 2-methylbut-1-en-4-ol, 1-ethynylcyclohexanol, 2-methoxyethanol, 2-ethoxyethanol, 3-methoxypropanol, 2-methoxyisopropanol, 3-methoxybutanol, methoxy-tert.- butanol, benzyl alcohol, α-phenylethanol and β-phenylethanol.

The starting materials II can be reacted with a stoichiometric amount or excess of the starting materials III, preferably using a ratio of from 1 to 15 moles, especially from 4 to 12 moles, of starting material III per mole of starting material II.

The reaction is generally carried out at from −40° to +125° C., preferably from −10° to +70° C. and especially from 0° to 60° C., under atmospheric or superatmospheric pressure, continuously or batchwise. Solvents which are inert under the reaction conditions are advantageously used. Examples of suitable solvents are halohydrocarbons, especially chlorinated hydrocarbons, e.g. tetrachloroethylene, 1,1,2,2- or 1,1,1,2-tetrachloroethane, amyl chloride, cyclohexyl chloride, dichloropropane, meth ne chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane; ethers, e.g. ethyl propyl ether, methyl tert.-butyl ether, n-butyl ether ether, di-n-butyl ether, diisobutyl ether, diisoamyl ether, diisopropyl ether, anisole, phenetole, cyclohexylmethyl ether, diethyl ether, ethylene glycol dimethyl ether, tetrahydrofuran, dioxane, thioanisole and β,β'-dichlorodiethyl ether; nitro-hydrocarbons, e.g. nitromethane, nitroethane, nitrobenzene, o-, m- and p-chloronitrobenzene and o-nitrotoluene; nitriles, e.g. acetonitrile, butyronitrile, isobutyronitrile, benzonitrile and m-chlorobenzonitrile; aliphatic or cycloaliphatic hydrocarbons, e.g. heptane, pinane, nonane, o-, m- or p-cumene, gasoline fractions boiling at from 70° to 190° C., cyclohexane, methylcyclohexane, decalin, petroleum ether, hexane, light naphtha, 2,2,4-trimethylpentane, 2,2,3-trimethylpentane, 2,3,3-trimethylpentane and octane; and appropriate mixtures. The solvent is advantageously used in an amount of from 100 to 2,000 percent by weight, preferably from 200 to 600 percent by weight, based on starting material II.

The reaction is advantageously carried out in the presence of an acid-binding agent, as a rule a basic compound, which is advantageously used in an amount of from 0.6 to 1.1, preferably from 0.8 to 1, equivalent per mole of starting material II. Preferred basic compounds are tertiary amines, alkaline earth metal compounds, ammonium compounds and especially alkali metal compounds, and appropriate mixtures. However, zinc comounds may also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethylene-glycollate, sodium 1,2-propylene-glycollate, sodium 1,3-propylene-glycollate, sodium diethylene-glycollate, sodium triethylene-glycollate, sodium 1,2-dipropylene-glycollate, potassium methylate, potassium ethylate, potassium n-propylate, potassium isopropylate, potassium n-butylate, potassium isobutylate, potassium sec.-butylate, potassium tert.-butylate, potassium ethylene-glycollate, potassium 1,2-propylene-glycollate, potassium 1,3-propylene-glycollate, potassium diethylene-glycollate, potassium triethylene-glycollate and potassium 1,2-dipropylene-glycollate; trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine. Instead of using an acid-binding agent, the hydrogen halide formed can also be removed by means of an inert gas, for example nitrogen.

The reaction may be carried out as follows: a mixture of starting material II and III, with or without a basic compound and/or a solvent, is kept at the reaction temperature for from 0.5 to 6 hours. It is possible to mix the starting material III or the starting material II with the solvent and then to add the other components. The end product I is isolated from the reaction mixture in the conventional manner, as a rule by filtration and fractional distillation.

In a preferred embodiment of the process of the invention, the starting material II is mixed with the starting material III in an inert solvent for from 2 to 30 minutes at from +10° to +40° C. and the acid-binding agent is then added at from −10° to +50° C., preferably from 0° to +30° C. To complete the reaction, the mixture is stirred further for from 0.5 to 4 hours at from 20° to 120° C., preferably from 30° to 60° C. The end product is then isolated in the above manner.

The new compounds which may be manufactured by the process of the invention are valuable starting materials for the manufacture of crop protection agents, dyes and pharmaceuticals. Thus, by eliminating alcohol in the α,β-position to the nitrogen, the end products I of the invention may be converted into unsaturated compounds of the formula

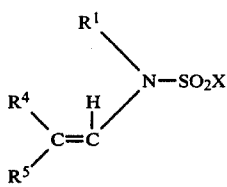

where $R^1$ is an aliphatic or cycloaliphatic radical, $R^4$ and $R^5$ may be identical or different and each is hydrogen, halogen or an aliphatic radical and X is halogen; from these compounds herbicides may be manufactured by reaction with glycollic acid anilides (German Laid-Open Application DOS No. 2,351,608). By hydrolysis of the end products IV, the corresponding haloamines may be manufactured, and these are starting materials for chemotherapeutics for combating cancer and tumors (Ullmanns Encyklopädie der technischen Chemie, Volume 10, pages 773 et seq.). Using the processes disclosed in Arzneimittelforschung 12 (1962), 1,119 et seq., the end products IV are converted to N,N-bis-(α-haloalkyl) sulfamidohydrazones, which are active against sarcomas and carcinomas. Herbicidal sulfamic acid esters may be manufactured from the end products IV by reaction with 2-alkoxy-2,3-dihydro-3,3-dimethyl-5-hydroxy-benzofuran derivatives (German Laid-Open Application DOS No. 2,324,592). In addition, herbicidal sulfamides may be manufactured by reacting the end products I, of the invention, with 3-alkyl-2,1,3-benzothiadiazin-4-one-2,2-dioxide compounds.

In all these cases it is advantageous to use, from amongst the new end products I, the preferred sulfamic acid halides I mentioned above, especially N-methoxymethyl-N-methylsulfamic acid chloride, N-methoxymethyl-N-ethylsulfamic acid chloride, N-methoxymethyl-N-propylsulfamic acid chloride, N-methoxymethyl-N-cyclohexylsulfamic acid chloride, N-allyloxymethyl-N-methylsulfamic acid chloride, N-ethoxymethyl-N-methylsulfamic acid chloride and N-n-propoxymethyl-N-methylsulfamic acid chloride.

In the Examples which follow, parts are by weight.

EXAMPLE 1

A solution of 13.5 parts of sodium methylate in 110 parts of methanol is added, in the course of 15 minutes at from 0° to 5° C., to a mixture of 44.5 parts of N-chloromethyl-N-methylsulfamic acid chloride in 260 parts of benzene. The reaction mixture is then stirred for 2 hours at 25° C., after which the sodium chloride which has precipitated is filtered off. After removing the solvent under reduced pressure, distillation gives 29.1 parts (67% of theory) of N-methoxymethyl-N-methylsulfamic acid chloride of boiling point 84°–87° C./12 mbar and $n_D^{25}=1.4536$.

EXAMPLE 2

If 45 parts of a 30 percent strength by weight solution of sodium methylate in methanol are added to 44.5 parts of N-chloromethyl-N-methylsulfamic acid chloride as described in Example 1, but without using additional solvent, parts (61% of theory) of N-methoxymethyl-N-methylsulfamic acid chloride of boiling point 84°–87° C./12 mbar and $n_D^{25}=1.4536$ are obtained.

EXAMPLE 3

500 parts of methanol are added in the course of 2 minutes at 25° C. to a mixture of 400 parts of N-chloromethyl-N-methylsulfamic acid chloride and 1,000 parts of cyclohexane. 227 parts of triethylamine are then added in the course of 30 minutes at from 0° to 7° C. The reaction mixture is then stirred for one hour at 40° C., after which it is concentrated under reduced pressure. The hydrochloride which has precipitated is filtered off and the filtrate is distilled, giving 282 parts (72% of theory) of N-methoxymethyl-N-methylsulfamic acid chloride of boiling point 84°–87° C./12 mbar and $n_D^{25}=1.4536$.

EXAMPLE 4

146 parts of triethylamine are added to a mixture of 289 parts of N-chloromethyl-N-ethylsulfamic acid chloride in 600 parts of cyclohexane and 320 parts of methanol in the course of 10 minutes at from 0° to 8° C. and 10 minutes at from 8° to 25° C. The mixture is then stirred for one hour at 46° C., after which it is concentrated under reduced pressure. After removing precipitated hydrochloride, and distilling the filtrate, 197 parts (70% of theory) of N-methoxymethyl-N-ethylsulfamic acid chloride of boiling point 93° C./11 mbar and $n_D^{25}=1.4558$ are obtained.

EXAMPLE 5

(a) 26 parts of sodium methylate in 160 parts of methanol are added in the course of 20 minutes, at from 0° to 5° C., to a mixture of 106 parts of N-chloromethyl-N-propylsulfamic acid chloride in 200 parts of cyclohexane. The reaction mixture is then stirred for one hour at from 40° to 45° C., after which the sodium chloride which has precipitated is separated off. On subsequent distillation, the solvent is removed first and 70.5 parts (68% of theory) of N-methoxymethyl-N-propylsulfamic acid chloride of boiling point 59°–65° C./0.1 mbar and $n_D^{25}=1.4543$ are then obtained.

(b) On using 65.5 parts of dimethylcyclohexylamine instead of sodium methylate and 200 parts of n-hexane instead of cyclohexane, the same end product is obtained in the same yield and purity.

EXAMPLE 6

22 parts of 2,6-lutidine are added in the course of 15 minutes, at from −5° to +5° C., to a mixture of 50 parts of N-chloromethyl-N-cyclohexylsulfamic acid chloride in 110 parts of cyclohexane and 55 parts of methanol. The reaction mixture is stirred for 20 minutes at 25° C. and one hour at 45° C. After concentrating the solvent under reduced pressure and removing the hydrochloride which has precipitated, distillation gives 30 parts (60% of theory) of N-methoxymethyl-N-cyclohexylsulfamic acid chloride of boiling point 102°–106° C./0.01 mbar and $n_D^{25}=1.4857$.

EXAMPLES 7 TO 9

The reaction is carried out as described in Example 3, under the conditions listed in the Table which follows.

TABLE I

| Example | Parts | Starting material II | Parts | Starting material III | Parts | % of theory | End product | Boiling point °C./mbar |
|---|---|---|---|---|---|---|---|---|
| 7 | 106.9 | $CH_3{-}N(Cl{-}CH_2){-}SO_2Cl$ | 224 | $CH_2{=}CH{-}CH_2OH$ | 42 | 35 | $CH_3{-}N(CH_2{-}O{-}CH_2{-}CH{=}CH_2){-}SO_2Cl$ with CH_2 linker | 60–63/0.01 |
| 8 | 178 | $CH_3{-}N(Cl{-}CH_2){-}SO_2Cl$ | 240 | $C_2H_5OH$ | 96 | 51 | $CH_3{-}N(C_2H_5{-}O{-}CH_2){-}SO_2Cl$ | 93–98/11 |
| 9 | 178 | $CH_3{-}N(Cl{-}CH_2){-}SO_2Cl$ | 190 | $n{-}C_3H_7OH$ | 103 | 51 | $CH_3{-}N(n{-}C_3H_7{-}O{-}CH_2){-}SO_2Cl$ | 63–67/0.2 | scale of from 0 to 100, with 0=no damage and 100=complete destruction.

TABLE 2

| | Amount used kg/ha of active ingredient | Test plants and % damage (Post-emergence method, in a greenhouse) | | | | | | | | | | |
|---|---|---|---|---|---|---|---|---|---|---|---|---|
| | | Avena sat. | Glyc. max | Oryz. sat. | Amm. cocc. | Amar. retr. | Cyp. esc. | Ipom. spp. | Ludw. spp. | Sesb. exalt. | Sida spin. | Sin. alba |
| Active compound from Example 10 | 2.0 | — | 5 | 0 | 50 | 60 | 60 | 50 | 50 | 50 | 95 | — |
| | 4.0 | 0(+) | 15 | 0 | 60 | 60 | 70 | 90 | 75 | 60 | 95 | 100(+) |

0 = no damage    100 = complete destruction(+)    3 kg/ha of active ingredient

List of plant names

| Latin name | Abbreviation in table | English name |
|---|---|---|
| Avena sativa | Avena sat. | oats |
| Glycine max | Glyc. max | soy beans |
| Oryza sativa | Oryz. sat. | rice |
| Ammannia coccinea | Amm. cocc. | redstem |
| Amaranthus retroflexus | Amar. retr. | pigweed |
| Cyperus esculentus | Cyp. esc. | yellow nutsedge |
| Ipomoea spp. | Ipom. spp. | morning glory |
| Ludwigia spp. | Ludw. spp. | — |
| Sesbania exaltata | Sesb. exalt. | hemp sesbania (coffeeweed) |
| Sida spinosa | Sida spin. | teaweed (prickly sida) |
| Sinapis alba | Sin. alba | white mustard |

EXAMPLE 10

32 parts of N-methoxymethyl-N-ethylsulfamic acid chloride are added in the course of 10 minutes at 20° C., whilst stirring, to a solution of 47 parts of the 1-potassium salt of 3-isopropyl-2,1,3-benzothiadiazin-4-one-2,2-dioxide in 1,200 parts of acetonitrile. The reaction mixture is then stirred for 5 hours at 20° C. and 2 hours at 75° C. and concentrated under reduced pressure, after which the residue is taken up in 400 parts of methylene chloride. After extraction with 0.2 N sodium hydroxide solution and water, and drying, 3-isopropyl-1-N'-methoxymethyl-N'-ethylsulfamoyl-2,1,3-benzothiadiazin-4-one-2,2-dioxide of $n_D^{25} = 1.5300$ are obtained.

EXAMPLE 11 (Herbicidal Action)

A range of crop plants and of unwanted plants are treated in a greenhouse. The test plants, segregated according to species, are grown in plastic pots. When they have grown to from 2 to 15 cm, depending on the age and the habit of the species, emulsions of the end product I prepared in Example 10 are applied to the leaves by means of jets which produce a fine spray (post-emergence treatment). Water (300 liters per hectare) serves as the vehicle and dispersing medium. The action sets in rapidly. After one week, the crop plants show very little or no attack, whilst the unwanted plants are dying (Table 2). The results are rated on a

I claim:

1. Sulfamic acid halides of the formula

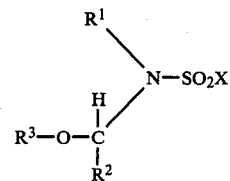

wherein $R^1$ is alkyl of 1 to 20 carbon atoms which may be unsubstituted or substituted by one or more halogen atoms in the β-, γ- and δ-positions, to the nitrogen, or is cycloalkyl of 4 to 8 carbon atoms, $R^2$ is hydrogen or is alkyl of 1 to 18 carbon atoms which is unsubstituted or substituted by one or more halogen atoms in the β-, γ- and δ-positions, to the nitrogen, $R^3$ is alkyl of 1 to 20 carbon atoms which is unsubstituted or substituted by 1 or 2 ether groups or by 1 or 2 halogen atoms or is alkenyl or alkynyl, of 2 to 20 carbon atoms, which is unsubstituted or substituted either by 1 or 2 ether groups or by 1 or 2 halogen atoms, or is cycloalkyl of 4 to 8 carbon atoms which is unsubstituted or substituted by one chlorine atoms or is aralkyl of 7 to 12 carbon atoms, and X is halogen, with the proviso that if $R^1$ is an aliphatic radical substituted by halogen in the β-position, $R^3$ is always one of said cycloaliphatic or araliphatic radical.

2. Sulfamic acid halides of the formula

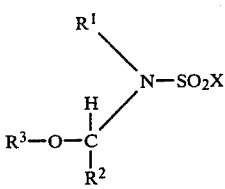

wherein $R^1$ is alkyl of 1 to 20 carbon atoms which may be unsubstituted or substituted either by one or more chlorine atoms or by one or more bromine atoms, or by both, in the β-, γ- and δ-positions, to the nitrogen, or is cycloalkyl of 4 to 8 carbon atoms, $R^2$ is hydrogen or is alkyl of 1 to 18 carbon atoms which is unsubstituted or substituted either by one or more chlorine atoms or by one or more bromine atoms, or by both, in the β-, γ- and δ-positions to the nitrogen, $R^3$ is alkyl of 1 to 20 carbon atoms which is unsubstituted or substituted by 1 or 2 ether groups or by 1 or 2 chlorine atoms or by 1 or 2 bromine atoms, or is alkenyl or alkynyl, of 2 to 20 carbon atoms, which is unsubstituted or substituted by 1 or 2 ether groups or by 1 or 2 chlorine atoms or by 1 or 2 bromine atoms, or is cycloalkyl of 4 to 8 carbon atoms which is unsubstituted or substituted by one chlorine atom or is aralkyl of 7 to 12 carbon atoms, and X is chlorine or bromine, with the proviso that if $R^1$ is an aliphatic radical which is substituted by halogen in the β-position, $R^3$ is always one of said cycloaliphatic or araliphatic radical.

3. A sulfamic acid halide of the formula

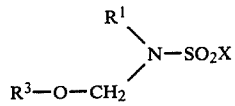

wherein $R^1$ is selected from the group consisting of methyl, ethyl, propyl and cyclohexyl, $R^3$ is selected from the group consisting of methyl, ethyl, and n-propyl and X is halogen.

4. The sulfamic acid halide of claim 3, in which $R^1$ is methyl, $R^2$ is hydrogen and $R^3$ is methyl.

5. The sulfamic acid halide of claim 3, in which $R^1$ is ethyl, $R^2$ is hydrogen and $R^3$ is methyl.

6. The sulfamic acid halide of claim 3, in which $R^1$ is propyl, $R^2$ is hydrogen and $R^3$ is methyl.

7. The sulfamic acid halide of claim 3, in which $R^1$ is methyl, $R^2$ is hydrogen and $R^3$ is ethyl.

8. The sulfamic acid halide of claim 3, in which $R^1$ is methyl, $R^2$ is hydrogen and $R^3$ is n-propyl.

9. N-Allyloxymethyl-N-methylsulfamic acid chloride.

* * * * *